United States Patent [19]
Borden et al.

[11] Patent Number: 6,072,187
[45] Date of Patent: Jun. 6, 2000

[54] APPARATUS AND METHOD FOR REDUCING STRAY LASER LIGHT IN PARTICLE SENSORS USING A NARROW BAND FILTER

[75] Inventors: Peter G. Borden, San Mateo; James B. Stolz, Fremont, both of Calif.

[73] Assignee: Fisher Pierce Co., Weymouth, Mass.

[21] Appl. No.: 08/271,311

[22] Filed: Jul. 6, 1994

[51] Int. Cl.[7] .................................................. G01N 21/00
[52] U.S. Cl. ...................................... 250/574; 356/339.11
[58] Field of Search ...................................... 250/574, 573, 250/575; 356/339, 339.11

[56] References Cited

U.S. PATENT DOCUMENTS

| | | | |
|---|---|---|---|
| 4,074,939 | 2/1978 | Rabl | 356/206 |
| 4,679,939 | 7/1987 | Curry et al. | 356/336 |
| 4,685,802 | 8/1987 | Saito et al. | 356/339 |
| 4,857,750 | 8/1989 | Millis et al. | 250/573 |
| 4,939,369 | 7/1990 | Elabd | 250/332 |
| 4,953,979 | 9/1990 | Hirako | 356/338 |
| 5,121,988 | 6/1992 | Blesener et al. | 356/442 |
| 5,305,073 | 4/1994 | Ford, Jr. | 356/338 |

*Primary Examiner*—Stephone Allen
*Attorney, Agent, or Firm*—Stoel Rives LLP

[57] ABSTRACT

A dark-field particle monitor and a method for reducing errors due to stray light in the particle monitor provides a particle monitor having (i) an optical element focussed on the laser beam for detecting particles and (ii) a filter for preferentially selecting light incident on said filter in a preferential direction. In one embodiments the filter is implemented by a narrow band filter having maximum transmission for light having a wavelength of the laser beam.

6 Claims, 3 Drawing Sheets

APPARATUS AND METHOD FOR REDUCING STRAY LASER LIGHT IN PARTICLE SENSORS USING A NARROW BAND FILTER

BACKGROUND OF THE INVENTION

1. Field of the Invention

The present invention relates to particle monitors. In particular, the present invention relates to dark-field particle monitors used in a manufacturing process.

2. Discussion of the Related Art

Dark-field particle monitors or sensors are often used in semiconductor processing equipment to monitor particle levels, which are critical to process yields. In a dark-field particle monitor or sensor, a particle passing through a collimated or focussed laser beam scatters laser light to a photocell located outside of the laser beam's direction of propagation. An example of such a particle sensor is described in U.S. Pat. No. 5,266,798 to P.Borden et al, entitled "High Sensitivity, Large Detection Area Particle Sensor for Vacuum Applications", Ser. No. 07/742,798, issued on Nov. 30, 1993, and filed on Aug. 8, 1991.

The performance of a dark-field sensor can be limited by a phenomenon known as stray or "DC" light. Stray light occurs when, as frequently happens, a sensor accumulates over time a coating or a film of dirt on the optical interfaces through which the laser beam passes. Naturally, this film of dirt scatters light ("stray light") from the laser beam. Because of the high intensity of the laser beam, the intensity of the stray light can be fairly high. Such stray light often illuminates the interior of the sensor housing, so that a portion of the stray light can find its way to the photodetector of the particle monitor.

Stray light limits the performance of the particle monitor in a number of ways. First, stray light is modulated by noise in the laser, so that strong stray light introduces the laser noise into the photodetector circuit, thereby causing inaccuracy in the particle count.

Second, although stray light intensity is normally relatively constant, so that the "DC" portion (i.e. low varying portion) of stray light intensity can be subtracted from the laser intensity detected by the particle monitor, a vibration in the particle detectors induces an "AC" component (i.e. high varying portion) in the intensity of stray light. This "AC" component results from stray light reflected off vibrating elements in the particle monitor. Particle monitors are highly sensitive to such an "AC" component, resulting in an erroneous particle count.

Third, stray light induces shot noise in the photodetectors of the particle monitor. Shot noise results from the statistical variation in the arrival rate of photons. The current $I_{noise}$, which is a noise current induced by stray light in a photodetector, is given by:

$$I_{noise} = \sqrt{2qBP_{stray}A}$$

where q is the charge of an electron, B is the bandwidth of the photodetector, $P_{stray}$ is the power of the incident stray light, and A is the conversion efficiency of the photodetector. The $I_{noise}$ current limits the signal-to-noise ratio of the photodetector, thereby limiting the photodetector's sensitivity to small particles.

For the above reasons, reduction in the incident intensity of stray light in particle monitors is highly desirable.

SUMMARY OF THE INVENTION

In accordance with the present invention, a method and a particle monitor configuration are provided to reduce erroneous particle counts due to stray light in a dark-field particle monitor. The present invention takes advantage of the fact that light scattered from a laser beam can be transmitted as parallel rays by a lens having a focus positioned on the laser beam where such scattering takes place. Accordingly, the present invention provides a dark-field particle monitor having (i) a laser beam passing through a region in which particles are to be monitored; (ii) a lens positioned to collect light scattered from the laser beam by the particles, the lens positioned such that a focus of the lens lies on the laser beam; (iii) a filter receiving the parallel rays at a preferential angle of incidence; and (iv) a detector to receive the filtered parallel rays.

In one embodiment, a particle monitor of the present invention includes a narrow band filter which provides maximum transmission for light having a wavelength of the laser beam. In that embodiment, the narrow band filter includes alternating layers of selenide and silicon dioxide materials provided on a glass substrate, where each of the alternating layers of selenide and silicon dioxide materials has a thickness approximating a wavelength of the laser beam divided by an index of refraction of that layer.

Under the present invention, stray light not radiating from the laser beam do not reach the filter at a preferred angle of incidence, and are not therefore not substantially transmitted to the detectors of the particle monitor. Hence, contribution by such stray light to the particle count is substantially eliminated. Further, by using a narrow band filter, error contributed by stray light not sharing the same wavelength of the laser beam is also substantially eliminated.

The present invention is better understood upon consideration of the detailed description below and the accompanying drawings.

DETAILED DESCRIPTION OF THE PREFERRED EMBODIMENTS

The present invention takes advantage of the unique properties of a laser beam used in particle monitors. Specifically, such a laser beam is highly monochromatic, and the region where particle scattering events of interest occur is relatively small. Thus, by properly applying optical filters, one can selectively detect light scattered from particles, and minimize errors due to stray light.

Figure 1:
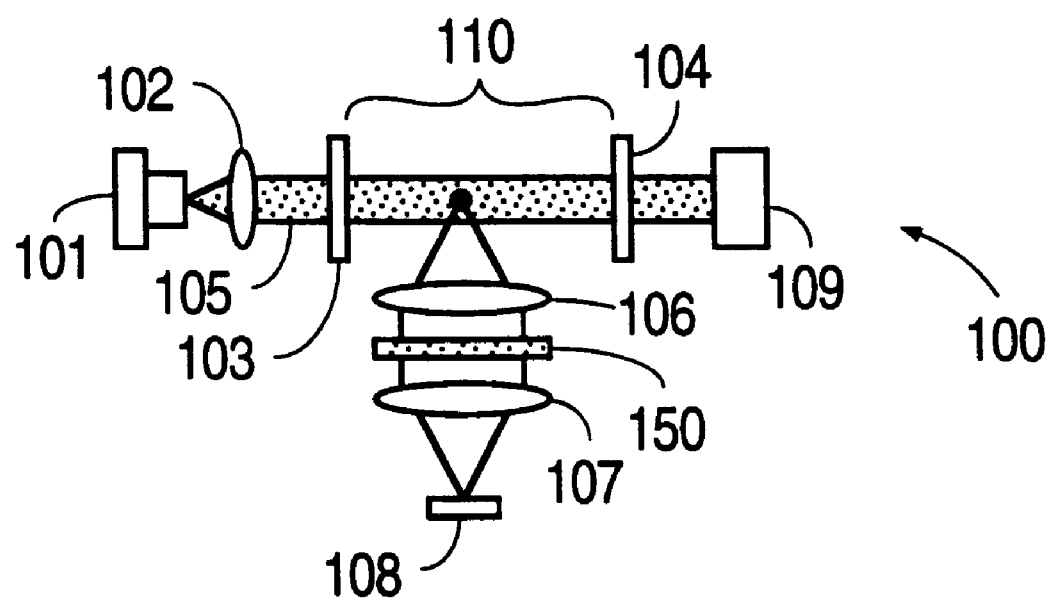
FIG. 1 shows the optical system of a dark field particle monitor 100 having a stray light filter 150, in accordance with the present invention.

FIG. 1 shows the optical system of a dark-field particle monitor 100, in accordance with the present invention. As shown in FIG. 1, a laser diode 101 in particle monitor 100 emits laser light and a collimating lens 102 focusses the laser light to form a laser beam 105. Laser diode 101 can be implemented by a laser diode such as the Sony 301V, available from Sony Corporation, Tokyo, Japan. In this configuration, an additional cylindrical lens (not shown) may also be inserted after collimating lens 102 to further focus laser beam 105, so as to achieve a higher beam intensity at or around the center of a detection region 110. Detection region 110, which is shown in FIG. 1 to be defined between windows 103 and 104, represents the region in which particles pass through laser beam 105.

In this embodiment, windows 103 and 104 are sapphire windows placed on ports in a vacuum pump line. In the configuration shown, particle monitor 100 can be used to measure particle levels in the exhaust stream of a vacuum processing system, such as a plasma etcher. Laser beam 105 impinges on beam stop 109, which completely absorbs laser beam 105 to prevent laser light from scattering back into particle monitor 100 to interfere with detection of laser light scattered by the particles in the vacuum pump line.

In this configuration, gas from a manufacturing process passes through laser beam 105 in region 110, flowing in a direction orthogonal to laser beam 105's direction of propagation. Particles carried in the gas scatter light from laser beam 105. A portion of the scattered light is collected by a collector lens 106. Collector lens 106 is positioned such that a focus of collector lens 106 lies on the trajectory of laser beam 105, so that scattered light rays emerging from collector lens 106 are approximately parallel. In this embodiment, a narrow band filter 150 filters the scattered light emerging from collector lens 106. The filtered light is then focussed by lens 107 onto photodetectors 108.

Figure 2:
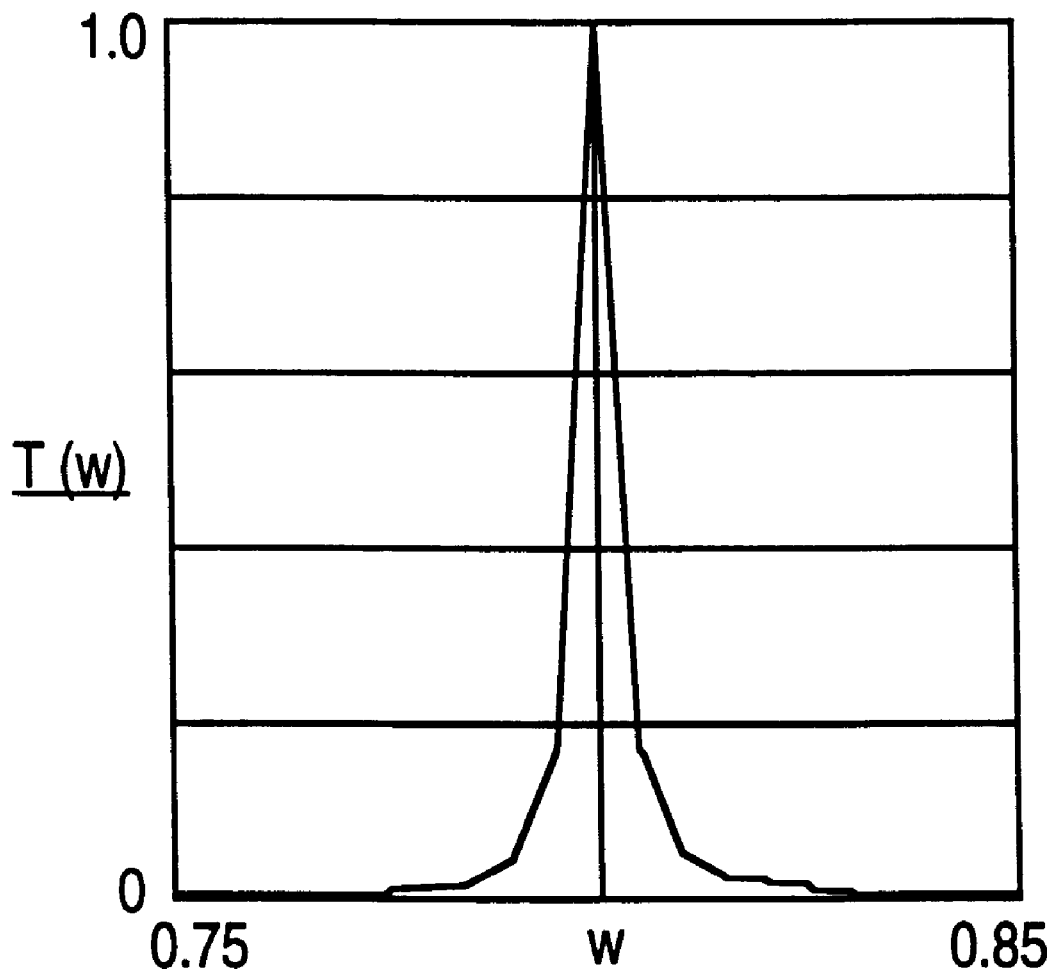
FIG. 2 is a graph showing the transmission characteristics of a narrow-band stray light filter for normally incident light.

Narrow band filter 150 is designed to provide maximum transmission at the wavelength of laser beam 105. The normalized transmission characteristics of narrow-band filter 150 for normally incident light is shown in FIG. 2. As shown in FIG. 2, substantially total transmission (i.e. approaching 1.0) is achieved at the wavelength of 800 nm. Transmission falls off quickly to less than 10% transmission outside of the range between 775 nm and 825 nm. The transmission characteristics of narrow band filter 150 can be achieved by coating on a glass substrate alternating dielectric layers of zinc selenide ("H layer"), which has an index of refraction of 2.35, and silicon dioxide ("L layer"), which has an index of refraction of 1.46. Each layers of zinc selenide or silicon dioxide has a thickness which is equal to one quarter of the laser wavelength divided by the index of refraction. The glass substrate has an index of refraction of 1.5.

In this embodiment, the pattern of the alternating dielectric layers is (HLHLHLHL)HH(LHLHLHLH). Because transmission at the wavelength of laser beam 150 approaches 1.0, the performance of particle monitor 100 is unaffected by the inclusion of narrow band filter 150.

Figure 3:
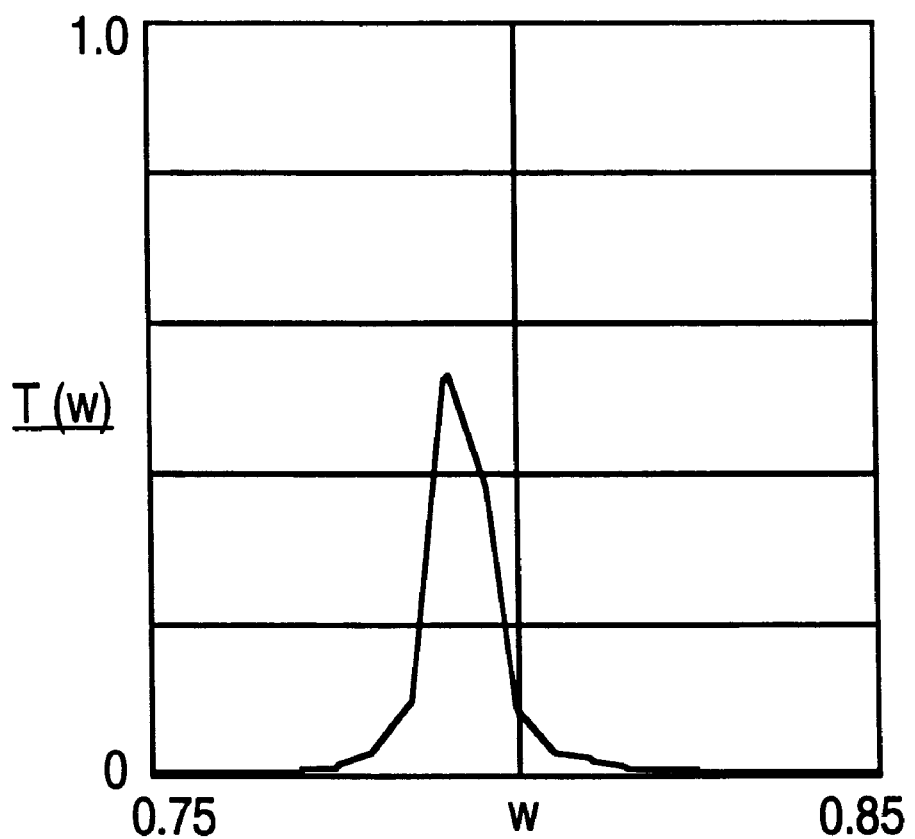
FIG. 3 is a graph showing the transmission characteristics of the narrow-band stray light filter of FIG. 2 for light incident at an angle of 15°.

Narrow band filter 150's transmission characteristics with respect to light not normally incident on its surface are useful for the present invention. FIG. 3 shows narrow band filter 150's transmission characteristics of rays impinging on narrow band filter 150 at an angle of incidence of 15°, for the same range of wavelengths as shown in FIG. 2. As shown in FIG. 3, at such an angle of incidence, transmission at 800 nm (i.e. the wavelength of laser beam 105) is reduced by about 90%, as compared to normally incident rays. Thus, from the transmission characteristics of FIGS. 2 and 3, it is evident the narrow band filter 150 preferentially select for transmission normally incident rays.

Since stray light is typically scattered into region 110 off fixtures within the housing of particle monitor 100, the bulk of such stray light does not emit from the focus of collector lens 106. Consequently, rays of such stray light do not emerge parallel from collector lens 106, so that such stray light would not impinge on narrow band filter 150 normally. As a result, the bulk of such stray light is not transmitted by narrow band filter 150. Thus, narrow band filter 150 is effective in reducing the level of stray light that reaches photodetector 108. Experiments using a particle sensor of the configuration shown in FIG. 1, i.e. when narrow band filter 150 is included, show a stray light reduction at photodetector 108 on the order of 75%.

The above detailed description is provided to illustrate the specific embodiments of the present invention, and is not to be taken as limiting. Numerous variations and modifications within the scope of the present invention are possible. The present invention is set forth in the following claims.

We claim:

1. A method for reducing errors due to stray light in a particle monitor, said particle monitor detecting light scattered from a laser beam by particles, said method comprising:

positioning a lens in said particle monitor to collect said light scattered from said laser beam, said lens positioned such that a focus of said lens lies on said laser beam, so that said light scattered from said laser beam emerges from said lens as parallel rays;

positioning a filter to filter said parallel rays, said filter having a preferential angle of incidence, wherein said filter provides maximum transmission of a selected wavelength of said laser beam at said angle of incidence; and positioning a detector to receive said filtered parallel rays.

2. A method as in claim 1, further comprising the step of positioning a second lens between said filter and said detector for focusing said filtered parallel rays onto said detector.

3. A particle monitor comprising:

a laser beam passing through a region in which particles are to be monitored;

a first lens positioned to collect light scattered from said laser beam by said particles, said first lens positioned such that a focus of said first lens lies on said laser beam, so that said light scattered from said laser beam emerges from said first lens as parallel rays;

a filter receiving said parallel rays, said filter having a preferential angle of incidence, wherein said filter provides maximum transmission of a selected wavelength of said laser beam at said angle of incidence; and a detector to receive said filtered parallel rays.

4. A particle monitor as in claim 3, further comprising a second lens positioned between said filter and said detector for focusing said filtered parallel rays onto said detector.

5. A particle monitor as in claim 3, wherein said filter comprises alternating layers of zinc selenide and silicon dioxide materials provided on a glass substrate.

6. A particle monitor as in claim 5, wherein each of said alternating layers of selenide and silicon dioxide materials has a thickness approximating a wavelength of said laser beam divided by an index of refraction of said layer.

* * * * *